US009408810B2

(12) United States Patent
Conover

(10) Patent No.: US 9,408,810 B2
(45) Date of Patent: Aug. 9, 2016

(54) ORAL ODOR CONTROL METHOD AND PRODUCT

(75) Inventor: Donald Conover, Buffalo Grove, IL (US)

(73) Assignee: Belle-Aire Frangrances, Inc., Mundelein, IL (US)

( * ) Notice: Subject to any disclaimer, the term of this patent is extended or adjusted under 35 U.S.C. 154(b) by 0 days.

(21) Appl. No.: 13/083,187

(22) Filed: Apr. 8, 2011

(65) Prior Publication Data

US 2011/0293668 A1 Dec. 1, 2011

Related U.S. Application Data

(60) Provisional application No. 61/350,306, filed on Jun. 1, 2010.

(51) Int. Cl.
| | |
|---|---|
| *A61K 31/00* | (2006.01) |
| *A61K 8/33* | (2006.01) |
| *A61K 8/35* | (2006.01) |
| *A61K 8/27* | (2006.01) |
| *A61Q 11/00* | (2006.01) |
| *A61K 8/92* | (2006.01) |

(52) U.S. Cl.
CPC . *A61K 31/00* (2013.01); *A61K 8/27* (2013.01); *A61K 8/33* (2013.01); *A61K 8/35* (2013.01); *A61K 8/922* (2013.01); *A61Q 11/00* (2013.01)

(58) Field of Classification Search
CPC .. A61K 9/0014; A61K 45/06; A61K 2300/00
USPC ........................................................ 424/400
See application file for complete search history.

(56) References Cited

U.S. PATENT DOCUMENTS

| | | | |
|---|---|---|---|
| 4,041,149 A | 8/1977 | Gaffar et al. | |
| 4,409,202 A | 10/1983 | Witzel et al. | |
| 4,512,968 A | 4/1985 | Komiyama et al. | |
| 4,689,214 A * | 8/1987 | Niles et al. | 424/49 |
| 4,689,215 A | 8/1987 | Ratcliff | |
| 4,814,164 A | 3/1989 | Barth et al. | |
| 4,959,204 A | 9/1990 | Ryan | |
| 5,149,521 A | 9/1992 | Hirose et al. | |
| 5,286,479 A | 2/1994 | Garlich et al. | |
| 6,197,288 B1 * | 3/2001 | Mankoo | 424/76.1 |
| 6,514,489 B1 | 2/2003 | Shacknai et al. | |
| 6,579,513 B1 * | 6/2003 | Tashjian et al. | 424/54 |
| 6,649,175 B1 | 11/2003 | Haslwanter et al. | |
| 6,664,254 B1 | 12/2003 | Rogozinski | |
| 6,905,675 B2 | 6/2005 | Shacknai et al. | |
| 7,311,900 B2 | 12/2007 | Conover | |
| 7,422,012 B2 | 9/2008 | Pinns | |
| 2002/0090386 A1 | 7/2002 | Haslwanter et al. | |
| 2002/0119106 A1 | 8/2002 | Harper et al. | |
| 2002/0164381 A1 | 11/2002 | Shacknai et al. | |
| 2002/0197287 A1 | 12/2002 | Streit et al. | |
| 2003/0133959 A1 | 7/2003 | Shacknai et al. | |
| 2003/0165439 A1 | 9/2003 | DePierro et al. | |
| 2003/0175216 A1 | 9/2003 | Rosenberg | |
| 2004/0057972 A2 | 3/2004 | Shacknai et al. | |
| 2004/0191206 A1 | 9/2004 | Cole et al. | |
| 2004/0265247 A1 | 12/2004 | Abiru et al. | |
| 2004/0266857 A1 * | 12/2004 | Jiang et al. | 514/437 |
| 2005/0175578 A1 | 8/2005 | Conover | |
| 2006/0045857 A1 | 3/2006 | Roszell | |
| 2006/0204558 A1 | 9/2006 | Kantner et al. | |
| 2006/0246021 A1 | 11/2006 | Roszell | |
| 2006/0251597 A1 | 11/2006 | Yu et al. | |
| 2007/0031526 A1 | 2/2007 | Gupta | |
| 2007/0110791 A1 | 5/2007 | Myhra | |
| 2007/0237737 A1 | 10/2007 | Dann et al. | |
| 2009/0162443 A1 | 6/2009 | Anthony et al. | |
| 2009/0269297 A1 | 10/2009 | Conover, Sr. | |

FOREIGN PATENT DOCUMENTS

| | | | | |
|---|---|---|---|---|
| CH | WO 2007025401 A1 * | 3/2007 | | A61K 8/02 |
| EP | 1192939 | 4/2002 | | |
| EP | 2020256 | 2/2009 | | |
| GB | 2173701 A | 10/1986 | | |
| JP | 2008094772 A | 4/2008 | | |
| WO | 0023040 | 4/2000 | | |
| WO | WO 0023040 A1 * | 4/2000 | | A61K 8/19 |
| WO | 0160373 | 8/2001 | | |
| WO | 0202059 | 1/2002 | | |
| WO | 03051294 | 6/2003 | | |
| WO | 2005020970 | 3/2005 | | |
| WO | 2006028613 | 3/2006 | | |
| WO | 2006118638 | 11/2006 | | |
| WO | 2007025401 A1 | 3/2007 | | |
| WO | 2007120665 | 10/2007 | | |
| WO | 2008079898 | 7/2008 | | |
| WO | 2009085889 | 7/2009 | | |
| WO | 2009131748 | 10/2009 | | |

OTHER PUBLICATIONS

OM Complex Datasheet (online) Belle-Aire Fragrances, Inc., Aug. 4, 2009 (retrieved Jun. 2, 2011) Retrieved from the internet: <URL: www.belle-aire.com/omcomplex.html, entire web page.
Russian Patent Office Action dated Apr. 20, 2015(English translation).
Supplementary European Search Report, dated Aug. 28, 2015.

* cited by examiner

*Primary Examiner* — Michael B Pallay
(74) *Attorney, Agent, or Firm* — Clark Hill PLC

(57) ABSTRACT

A product and method for controlling mouth odor and bad breath using an oral care product containing an odor neutralizer. The product for use in oral care or for use in the mouth to control mouth odors includes an odor neutralizer compound. In a preferred method of manufacture, the O.M. COMPLEX oral compound is mixed into a concentrated flavor material. The concentrated flavor material is then added in small percentages to the product during manufacture so that the resulting product includes the odor neutralizer compound. The product may be used in the ordinary manner by a user and during use the O.M. COMPLEX oral compound serves to capture and neutralize odor causing compounds.

19 Claims, 1 Drawing Sheet

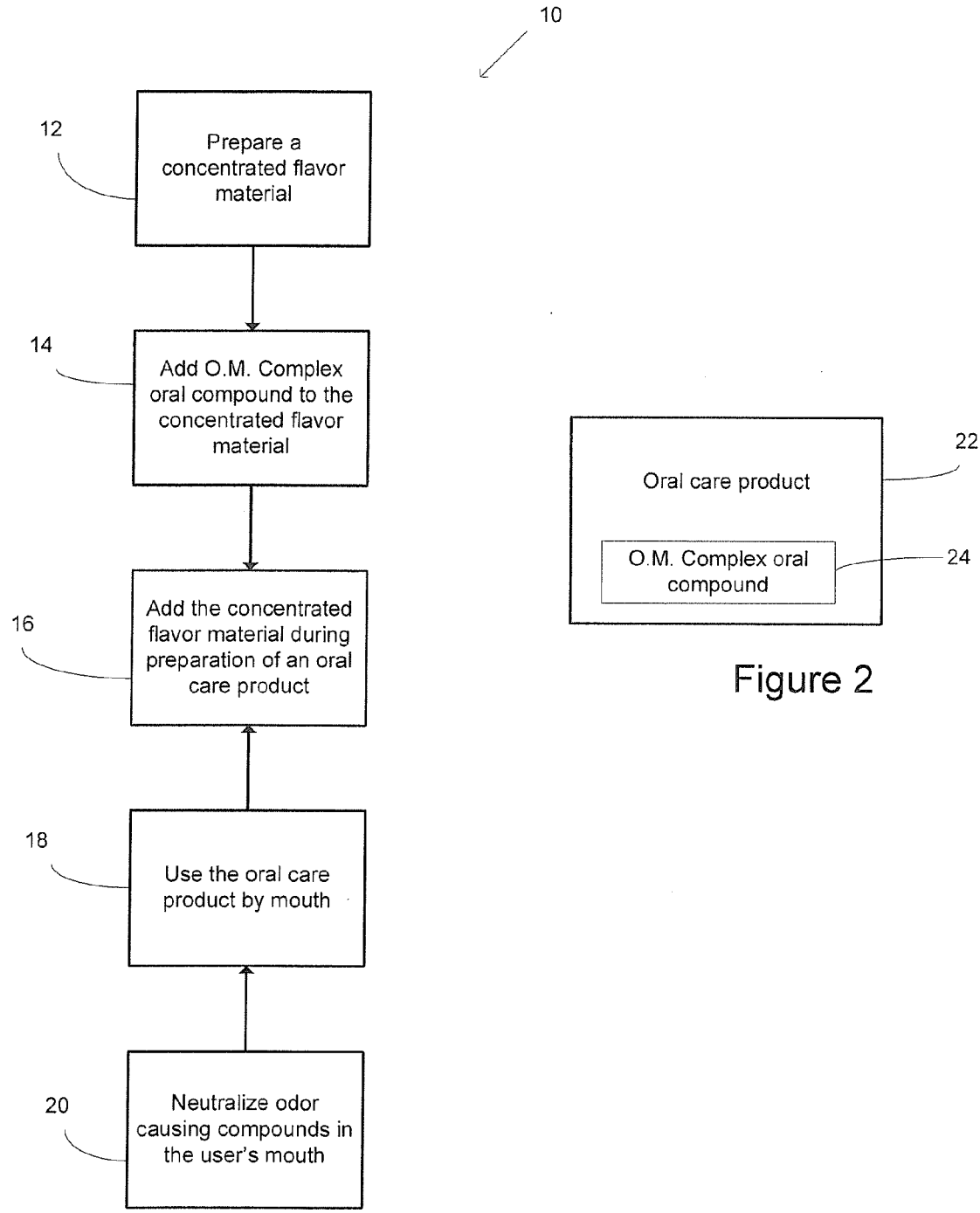

ORAL ODOR CONTROL METHOD AND PRODUCT

CROSS-REFERENCE TO RELATED APPLICATION

This application claims the benefit of U.S. Provisional Patent Application Ser. No. 61/350,306, filed Jun. 1, 2010, which is incorporated herein by reference.

BACKGROUND OF THE INVENTION

1. Field of the Invention

The present invention relates generally to method and product to control malodors from a human mouth, and in particular to an oral care product and method for use by a human, wherein the oral care product includes an odor neutralizer.

2. Description of the Related Art

Mouth odors, also referred to as halitosis or bad breath, is a common problem which has many possible causes and for which many solutions have been proposed. Products used to address bad breath include toothpastes, mouth washes and mouth rinses, tongue scrapers, chewing gum, breath mints, breath sprays, as well as home made solutions such as baking soda, hydrogen peroxide, leafy plants such as parsley, and other items and materials. Although solutions can lie in improved dental care and avoidance of certain foods, many mouth odors are merely masked by flavored products being offered on the market.

It would be a benefit if mouth odors, and in particular malodors or bad breath, were addressed by a product that neutralizes the odor rather than merely masking the odor.

SUMMARY OF THE INVENTION

The present invention provides a method and product for addressing the problem of bad breath or mouth odors by neutralizing malodor molecules in the mouth and emitted from the mouth. An odor neutralizing agent is incorporated into a mouth care product so that as the person uses the mouth care product the odor neutralizing agent has an opportunity to eliminate or neutralize the malodor. The mouth care product may be a product kept in the mouth for a short period, such a mouth rinse or toothpaste, or a product that is kept in the mouth for a longer time, such as a lozenge or chewing gum. The user may use the mouth care product in the normal way and, while the product is being used, the odor neutralizing agent captures malodor molecules in the mouth so as to reduce or eliminate the malodor.

The method in an alternate embodiment provides that the mouth care product incorporating the odor neutralizing agent may be used in a different or non-traditional way than is typical for the product, which is also encompassed within the present invention.

Embodiments of the present invention also provide a product, such as a mouth care product, that incorporates an odor neutralizing agent. The product may be any of a variety of products such as products for oral or dental care including mouth rinse, mouthwash, and tooth paste, as well as products used more for odor control including lozenges, breath mints, breath freshening wafers, chewing gum, and the like. The product may also be a nasal care product or even an ingestible product. The odor neutralizing agent is incorporated into the product in an effective amount so that, as the user uses the product, the neutralizing agent captures and thereby eliminates the bad odor causing capability of the malodor compounds.

Embodiments of the present invention also provide a method of manufacture for products used to reduce or eliminate mouth odors. In one such embodiment, concentrated flavoring agents are provided with a quantity of an odor neutralizing agent. The concentrated flavor material with the odor neutralizing agent therein is mixed into the materials during manufacture of the mouth care product so that the resulting product includes not only the flavoring agent but also the odor neutralizing agent. The flavoring agent with the neutralizing agent may be provided in the usual quantities for flavoring agents during the manufacture of the product.

BRIEF DESCRIPTION OF THE DRAWINGS

FIG. 1 is a flow chart of steps in an embodiment of the method according to the principles of the present invention;

FIG. 2 is a schematic illustration of a product according to the present invention; and Appendix sheets 1 and 2 show chemical diagrams of examples of compounds according to the principles of the present invention.

DETAILED DESCRIPTION OF THE PREFERRED EMBODIMENTS

Referring now to the drawings, there is shown in FIG. 1 a method 10 for manufacture and use of a product for control of mouth odors. In a first step 12, a flavoring agent is provided in highly concentrated form. Alternately, the flavoring agent may be prepared in a lower concentration or diluted form. Any flavor is possible, although peppermint, spearmint, wintergreen, cinnamon, bubblegum, anise and fruit flavors are popular. More exotic or unusual flavors are also possible including chocolate, peanut butter, pine, tea, fennel, lavender, ginger, neem, or vanilla. The flavoring agent may be any known flavoring agent as used in mouth care products or in products used in the mouth. Instead of a flavoring agent, the present method may provide other materials or components which are used in the manufacture of mouth care products. For example, the method may provide that a base material, binder, thickener, preservative or other material or components used to manufacture oral care products is provided in the first step.

In step 14, an odor neutralizing compound is added to the flavoring agent or other material. The odor neutralizing compound of a preferred embodiment is the O.M. COMPLEX oral compound, a proprietary product of Belle-Aire Fragrances, Inc. The O.M. COMPLEX oral (a trademark of Belle-Aire Fragrances, Inc.) compound in one embodiment is mixed into the concentrated flavoring agent at an amount of 0.20-5.00% O.M. COMPLEX oral compound by volume to the remainder of flavoring concentrate. Other concentrations are possible, depending on other factors, such as the concentration level of the flavoring agent.

In step 16, the concentrated flavoring agent which includes the odor O.M. COMPLEX oral compound is used as a component in the manufacture of oral care products. For instance, the flavoring agent may be added at the usual time and in the usual percentage or quantity and in the usual way as flavoring agents in known oral care products. The concentrated flavoring agent is typically added in a small percentage to provide the dominant flavor for the product. In the present method, the flavoring agent with the odor O.M. COMPLEX oral compound is added to flavor the product, although other materials containing the odor O.M. COMPLEX oral compound may be used in the manufacture of the oral care product instead. The product produced according to step 16 may include oral care products, which includes oral use products, such as mouthwash, mouth rinse, toothpaste, lozenges, breath mints, breath sprays, breath wafers, and chewing gum by adding the flavoring agent with the O.M. COMPLEX oral compound at about 0.20% to 5.00% per volume. The resulting level of O.M. COMPLEX oral compound in the product is preferably in the range of 0.00020 to 0.01% per volume. This is just one example, and other levels of O.M. COMPLEX oral compound in the product may be provided as well. For example, the O.M. COMPLEX oral compound may range from 0.000001 to 0.000006 per volume, or 1 to 6 P.P.M. in the oral care product. Other ranges are contemplated according to the principles of the present invention. The O.M. COMPLEX oral compound may be added to or incorporated into an oral care product with or without flavoring agents or components. For example, it is within the scope of the present invention to provide the O.M. COMPLEX oral compound in an oral care product manufactured with a natural flavoring agent that has not been added in highly concentrated form. For products such as toothpicks, tooth brushes, dental floss, oral swabs, tongue scrapers or tongue cleaners and other non-liquidous products, the odor neutralizing compound may be provided as a coating on the product, or by impregnating a porous product body with the neutralizing compound, or otherwise carrying the neutralizing compound into the mouth.

The oral care product that includes the odor O.M. COMPLEX oral compound is provided to users. The oral care product may be toothpaste, mouthwash or rinse, chewing gum, breath mints, candies, lozenges, breath sprays, breath wafers, tooth picks, tooth brushes, tongue cleaners or scrapers, or other products. The products may be provided for the primary purpose of mouth odor control or for some other primary purpose, including tooth cleaning, fluoride treatment, food residue removal, plague removal, tooth stain removal, etc. A schematic representation of an oral care product is shown in FIG. 2, wherein the product is indicated by reference number 22 and the odor encapsulating compound in the product is indicated as 24.

The user uses the oral care product 22 as shown at step 18 of FIG. 1. The use may be according to the customary use of the product, such as rinsing with a mouth rinse, chewing a chewing gum product, brushing the user's teeth with a toothpaste product, or dissolving a lozenge in the mouth. The oral care product 22 may be used for a longer or shorter period of time than customary, or used in a different way than customary, according to variations in the present method.

During and/or following use of the oral care product 22, the odor O.M. COMPLEX oral compound acts to neutralize the odor causing compounds, so that the user's bad breath is neutralized, as indicated at step 20 in FIG. 1.

The present invention relates to an oral compositor for the control of oral malodors. Oral compositor refers to a complex application to the oral cavity to clean and deodorize the teeth and oral cavity surfaces. Oral malodor is caused by the activity of microorganisms on dental plaque adhering to salivary elements to produce sulfur compounds. These sulfur compounds consist of V.S.C. (volatile sulfur compounds) such as hydrogen sulfide ($H_2S$), methyl mercaptane (($CH_3$)SH), and dimethyl sulfide (($CH_3$)2S) and others. Previous methods of inhibiting the volatile sulfur compounds (V.S.C.) to reduce oral malodor have been antimicrobials such as cetyl pyridim chloride and triclosan. These antimicrobials can cause staining of the teeth & absorption on the soft tissue In the mouth. An oral composite (O.M. COMPLEX oral) containing natural and related aromatics with zinc complexes act in a synergistic way, so that mouth malodor is eliminated. Cysteine and methionine are sulfur containing amino acids that serve as substrates for bacteria producing volatile sulfur compounds in the mouth. It is believed that the O.M. COMPLEX oral with it affinity for volatile sulfur compounds (V.S.C.) such as $H_2S$, ($CH_3$)SH, and ($CH_3$)2S inhibits the generation of V.S.C. precursors. O.M. COMPLEX oral reacts with thiol groups of volatile sulfur compounds (V.S.C.) therefore neutralizing their effect by producing non-volatile components.

The present invention relates to an oral composition for controlling mouth malodor consisting of an oral composition consisting essentially of an orally acceptable vehicle (in one example, a flavor) containing a O.M. COMPLEX of about 0.0025% to 5.00%. The composition is as follows ionones, alpha, beta, and gamma (see Appendix sheet 1) containing a carbonyl group. The term ionone includes isomeric forms and forms of ionones such as irone (see Appendix sheet 2). Aldhydes such as cyclamen aldehyde (see Appendix sheet 1) at levels of 0.02% to 10.00% and naturals such as oil of cardamom, orris, and violet at levels of 0.002% to 0.10% may be included. The natural and related aromatics with the addition of zinc complexes useful in the present method are oil of cardamom, oil of violet leaves, orris concrete, ionone, irone, cyclamen aldehyde, zinc acetate, zinc citrate (see Appendix sheet 2), zinc lactate (see Appendix sheet 2), and zinc gluconate (see Appendix sheet 2).

The compounds known as O.M. COMPLEX oral has the ability to neutralize volatile sulfur compound (V.S.C.) in the mouth where oral malodor is present at levels 200-300 PPB and even as high as 350-400 PPB. These levels are considered noticeable by an observer standing several feet away from the patient or other person. Flavoring agents may be added to O.M. COMPLEX oral compound in the product. Suitable flavoring agents include oil peppermint, oil spearmint, oil clove, oil wintergreen, and oil sassafras. Sweetening agents which can be used, including sweetening agents such as include aspartame, saccharin, and dextrose. Flavoring and sweetening agents may be used in the oral care product at levels of 0.002%-3.0% by weight.

The combination of ionone, irone, and cyclamen aldehyde with the addition of zinc salts splits and naturals such as oil of cardamon, violet leaves, and orris absolute in a preferred embodiment has a synergistic effect by complexing and eliminating oral malodor for long periods of time depending on the individual.

A method of controlling mouth odor or bad breath, using an oral compound is provided. The oral compound may contain natural and related aromatics with the addition of zinc complexes. This composition may be used in conjunction with a flavoring agent at an appropriate level in the oral care product. The oral care product provides a breath neutralizing function, and may be in the form of mouth wash, toothpaste, powder tablet, pill, dental cream or chewing gum. The O.M. COMPLEX oral neutralizer is effective against hydrogen sulfide, methyl mercaptan and dimethyl sulfide, as well as potentially other volatile sulfur compounds (V.S.C.)

The O.M. COMPLEX oral component of the product operates to provide molecular nucleophilic substitution of odor causing chemicals, particularly those that include a sulfur component. For instance, the product with the O.M. COMPLEX oral component neutralizes materials known to cause mouth odors, such as hydrogen sulfide, dimethyl sulfide, other sulfur compounds, methyl mercaptan and other captals, thiazine, cadaverine, putrescine, skatole, isovaleric acid, as well as others. The mouth odors may arise from a combination of one of these compounds or from two or more of the compounds. These odor causing compounds arise in the mouth and below the gum line as a result of anaerobic conditions and are produced by anaerobic bacteria and/or food residue. Malodors may also arise in the digestive tract. Odor causing compounds may also originate in the nasal or sinus cavities, throat, or other areas of the person. An oral use product as provided herein is capable of reducing or eliminating any such odors that are expelled by mouth.

The product containing the O.M. COMPLEX oral compound is used by a patient or other person, such as by using mouth wash, tooth paste, chewing gum, an oral swab, mouth sprays or other products containing the O.M. COMPLEX oral compound, causing the O.M. COMPLEX oral compound in the product to come into contact with the odor causing compounds in the mouth so that substitution reactions occurs between the O.M. COMPLEX oral compound and the odor causing compounds. The contact may be by direct physical contact of the oral care product with mouth surfaces on which the odor causing compounds are disposed, by contact with the odor causing compounds in liquid suspension or otherwise carried by liquids in the mouth, or by contact with airborne compounds. The odor neutralizing effect may be accelerated by agitation of the oral care product in the mouth by the user, such as by swishing the oral care product around the inside of the mouth or by brushing or swabbing the product in the mouth. Odors are neutralized as well by still or relatively still contact between the compounds, such as may occur when a residue of the oral care product remains in the mouth. At least some of the oral care product containing the O.M. COMPLEX oral compound may remain in the mouth for a time as a coating or residue so that the neutralizing effect on the odor causing compounds occurs over an extended time after use of the oral care product.

It is also contemplated to provide the care product with the neutralizing compound as a nasal spray, nasal swab, nasal flush or other nasal cavity care product, or to provide the product as an ingestible product, for instance in the form of a pill or capsule, which acts within the digestive tract.

Contact between the oral care product and the odor causing compounds results in a reaction that chemically changes the character of the odor causing compound so that it no longer has the offensive odor. Alternately, the odor causing compound is captured by the O.M. COMPLEX oral compound. The user of the oral care product and those nearby are unable to smell the odor causing compounds as a result of the compounds being neutralized, or are they may be able to detect them but at greatly reduced levels. Any bad breath of the user is eliminated or greatly reduced, to the benefit of the user in social situations.

Many breath freshener products address problems of breath odor by bactericidal action or bacteriastatic action. The bacteria may reside in areas below the gum line, between teeth or other areas not reached by the bactericidal agent so that the bactericide is ineffective at killing the bacteria or removing the odor, and further even if the bacteria are killed their odor causing by-products may remain. The present product differs from such products by neutralizing the odor caused by the bacterial by-products, for example. The odor neutralization is through natural substation of at least a portion of one or more of the compounds that cause the offending odor, thereby providing a neutralizabilty action for odor control. Another way of describing the action of the present product is aromasticity.

The present odor O.M. COMPLEX oral compound of some embodiments do not contain bactericidal agents, whereas other embodiments of the O.M. COMPLEX oral compound may contain one or more bactericidal agents to both kill the bacteria that form the odor causing compounds and with the action of the O.M. COMPLEX oral compound to neutralize their odor causing compounds. The flavoring agent with which the O.M. COMPLEX oral compound is mixed in the oral care product, such as mint or other flavors, may serve to freshen the breath as well.

Products incorporating the O.M. COMPLEX oral component at the levels noted herein have proven safe, and the O.M. COMPLEX Oral component has been food grade approved, even if ingested.

Thus, there is shown and described an odor reducing product, a method for its manufacture and a method for its use.

Although other modifications and changes may be suggested by those skilled in the art, it is the intention of the inventors to embody within the patent warranted hereon all changes and modifications as reasonably and properly come within the scope of their contribution to the art.

I claim:

1. An oral care product, comprising:
a base oral care product; and
an odor neutralizing compound incorporated with said base oral care product, wherein the odor neutralizing compound includes a combination of ionone, irone, and cyclamen aldehyde with zinc salt and a natural, wherein the cyclamen aldehyde is 0.02 wt % to 10.00 wt % of the odor neutralizing compound and wherein the natural is at least one of oil of violet leaves and orris absolute, wherein the oil of violet leaves and orris absolute are collectively 0.002 wt % to 0.10 wt % of the odor neutralizing compound, the odor neutralizing compound is about 0.0025 wt % to about 5.00 wt % of the oral care product, the odor neutralizing compound has a chemical structure able to undergo molecular nucleophilic substitution upon contact with odor causing chemicals having a sulfur component to thereby neutralize malodors caused by the odor causing chemicals having the sulfur component, the oral care product being effective to neutralize malodors in the mouth upon use of the oral care product, the odor neutralizing compound being free of bactericidal agents.

2. An oral care product as claimed in claim 1, wherein said odor neutralizing compound is mixed into said base oral care product.

3. An oral care product as claimed in claim 2, wherein said base oral care product is a product selected from the group consisting of: mouth rinse, mouthwash, tooth paste, lozenges, breath mints, breath freshening wafers, and chewing gum.

4. An oral care product as claimed in claim 1, wherein said odor neutralizing compound is coated onto said base oral care product or impregnated into said base oral care product.

5. An oral care product as claimed in claim 4, wherein said oral care product is a product selected from the group consisting of: toothpicks, a tooth brush, dental floss, oral swab, tongue scraper, and tongue cleaner.

6. An oral care product as claimed in claim 1, wherein the zinc salt includes at least one of zinc acetate, zinc citrate, zinc lactate, and zinc gluconate.

7. An oral care product as claimed in claim 1, further comprising: a flavoring agent and a sweetening agent.

8. An oral care product as claimed in claim 7, wherein said flavoring agent is one of oil peppermint, oil spearmint, oil clove, oil wintergreen, and oil sassafras.

9. An oral care product as claimed in claim 7, wherein said sweetening agent is one of aspartame, saccharin, and dextrose.

10. An oral care product as claimed in claim 7, wherein said flavoring agent and said sweetening agent are in the oral care product at a level of 0.002 percent to 3.0 percent by weight.

11. The oral care product of claim 1, wherein the cyclamen aldehyde is 0.02 wt % to 1.00 wt % of the odor neutralizing compound.

12. The oral care product of claim 1, wherein the natural is 0.005 wt % to 0.100 wt % of the odor neutralizing compound.

13. An oral care product made by a process comprising the steps of:
    providing a flavoring agent having a flavor to be used in an oral care product;
    adding an odor neutralizing agent to the flavoring agent to provide a mixture of the flavoring agent with the odor neutralizing agent, wherein the odor neutralizing agent includes a combination of ionone, none, and cyclamen aldehyde with zinc salt and a natural, wherein the cyclamen aldehyde is 0.02 wt % to 10.00 wt % of the odor neutralizing compound and wherein the natural is at least one of oil of violet leaves and orris absolute, wherein the oil of violet leaves and orris absolute are collectively 0.002 wt % to 0.10 wt % of the odor neutralizing compound,
    the odor neutralizing agent has a chemical structure able to undergo molecular nucleophilic substitution upon contact with odor causing chemicals having a sulfur component to thereby neutralize malodors caused by the odor causing chemicals having the sulfur component, the odor neutralizing agent being free of a bactericidal agent; and
    adding the mixture to ingredients of an oral care product during manufacture of the oral care product to produce the oral care product, the oral care product being effective to neutralize malodors in the mouth upon use of the oral care product.

14. The oral care product of claim 13, wherein the cyclamen aldehyde is 0.02 wt % to 1.00 wt % of the odor neutralizing compound.

15. The oral care product of claim 13, wherein the natural is 0.005 wt % to 0.100 wt % of the odor neutralizing compound.

16. An oral care product, comprising:
    a base oral care product; and
    an odor neutralizing compound incorporated with said base oral care product, wherein the odor neutralizing compound comprises irone, one or more aldehydes, one or more naturals, and one or more zinc complexes, wherein the natural is one or more of oil of violet leaves and orris absolute, and wherein the aldehyde is cyclamen aldehyde, and wherein the zinc complex is one or more of zinc acetate, zinc citrate, zinc lactate, and zinc gluconate, wherein the cyclamen aldehyde is 0.02 wt % to 10.00 wt % of the odor neutralizing compound and wherein the oil of violet leaves and orris absolute are collectively 0.002 wt % to 0.10 wt % of the odor neutralizing compound, the odor neutralizing compound being free of bactericidal agent.

17. An oral care product as claimed in claim 16, wherein said odor neutralizing compound is about 0.0025 wt % to about 5.00 wt % of the oral care product.

18. The oral care product of claim 16, wherein the cyclamen aldehyde is 0.02 wt % to 1.00 wt % of the odor neutralizing compound.

19. The oral care product of claim 16, wherein the natural is 0.005 wt % to 0.100 wt % of the odor neutralizing compound.

* * * * *